United States Patent [19]

Bhuvaneshwar

[11] Patent Number: 4,822,355
[45] Date of Patent: Apr. 18, 1989

[54] HEART VALVE ASSEMBLY

[75] Inventor: G. S. Bhuvaneshwar, Trivendrum, India

[73] Assignee: Sree Chitra Tirunal Inst. for Medical Science & Technology, Kerala, India

[21] Appl. No.: 210,165

[22] Filed: Jun. 21, 1988

Related U.S. Application Data

[63] Continuation of Ser. No. 928,095, Nov. 7, 1986, abandoned.

[30] Foreign Application Priority Data

Aug. 21, 1986 [IN] India .................................. 671186

[51] Int. Cl.$^4$ .............................................. A61F 2/24
[52] U.S. Cl. ........................................ 623/2; 623/900
[58] Field of Search .................................. 623/2, 900

[56] References Cited

U.S. PATENT DOCUMENTS

| 4,057,857 | 11/1977 | Fettel | 623/2 |
| 4,263,681 | 4/1981 | Notton | 623/22 |
| 4,494,253 | 1/1985 | Bicer | 623/2 |
| 4,532,659 | 8/1985 | Kaster | 623/2 |
| 4,687,487 | 8/1987 | Hinterman | 623/22 |

Primary Examiner—Richard J. Apley
Assistant Examiner—James Prizant
Attorney, Agent, or Firm—Dennis P. Clarke

[57] ABSTRACT

Improved heart valve assembly 1(FIG. 4) includes:
Sewing ring 2 made preferably of woven/knitted fabric of carbon/carbon coated polyester/polytetra-fluoroethylene;
Metallic valve housing 3, with external groove accommodating sewing ring, with flat lugs 3a on one side and lug 3b having hook 3c on the other side, said housing being preferably made of "Stellite", titanium or alloys of titanium with aluminum, vanadium or palladium or of stainless steel or cobalt based alloys optionally with coating of boron nitride, titanium nitride or diamond and;
Valve occluder disc 4 made of Agate, polyacetal homopolymer, synthetic sapphire, synthetic ruby, corundum or ceramics like alumina, tungsten carbide, titanium carbide or their mixture or of metals like aluminum, titanium, steel or cobalt-chromium-tungsten alloy having coating of one or more of said ceramics, and tapered surface 4a with depression/groove 4c therein held by hook 3c on its less pronounced depression 4d as seen in FIG. 5 more clearly.

2 Claims, 1 Drawing Sheet

HEART VALVE ASSEMBLY

This is a continuation of application Ser. No. 928,095, filed Nov. 7, 1986, now abandoned.

BACKGROUND OF THE INVENTION

This invention relates to improvements in or relating to prosthetic devices.

This invention more in particular relates to prosthetic devices such as heart valve or what is called cardio-vascular valvular prosthesis and to a process for manufacturing such a cardio-vascular prosthesis.

Cardio-vascular prosthesis are already known and several types are available and a few have also been proposed. These devices have to a certain extent solved the problems faced by the medical profession and have thus been found to be suitable cardiac valves.

However, many problems are still faced by the presently known and proposed cardiac valves and there is more room for improvement.

SUMMARY OF THE INVENTION

For the sake of convenience, in the ensuing description, we have referred to the prosthetic devices or cardio vascular prosthesis as "heart valve assembly."

In general a heart valve assembly comprises a heart valve disc mounted tiltably on a mounting arrangement within a circular ring component of metal and is further provided with the fabric sewing ring held on the circular metal ring enabling the whole assembly to be stitched to the necessary part of the body. The disc is known as disc occluder, the mounting arrangement is called the valve house or cage. The valve housing is generally made of metal.

In the known art, heart valve assembly it has often been found that the disc occluder, though made of wear resistant material at times undergoes wear thereby upsetting the proper balance which results in malfunctioning and has to be replaced.

We invite special reference to heart valve assembly disclosed in U.S. Pat. No. 4,494,253 which is equivalent to Argentina Pat. No. 283040. This art discloses a heart valve assembly wherein the disc occluder is formed from a carbon substrate. Further the disc occluder is mounted within the metallic ring component in a tiltable manner on three supporting lugs within a semi circular portion of the ring component. Further two opposite lugs in the construction of the U.S. Patent face almost towards each other.

DETAILED DESCRIPTION OF THE PREFERRED EMBODIMENTS

Figure 1:
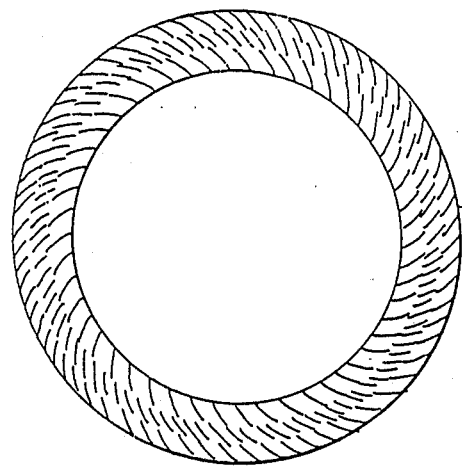
FIG. 1 is a plan view of sewing ring 2.
Figure 5:
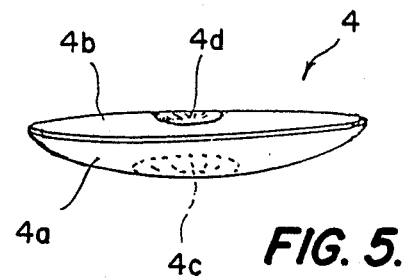
FIG. 5 is a side sectional view of the occluder disc.
Figure 2:
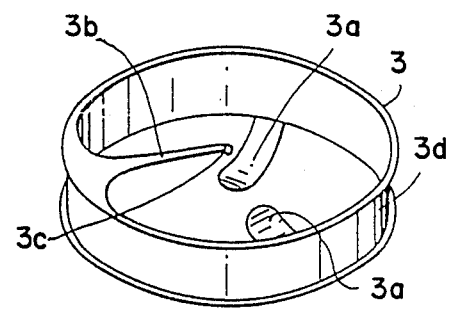
FIG. 2 is a prospective view of the valve housing.
Figure 3:
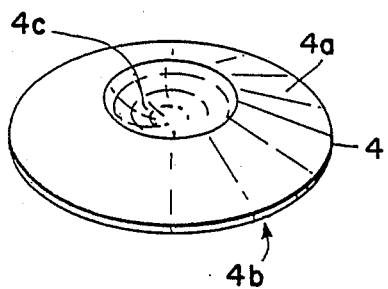
FIG. 3 is a view of the valve occluder disc.
Figure 4:
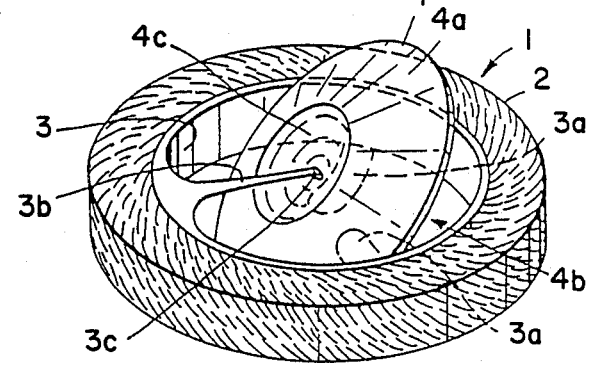
FIG. 4 is a view of the assembled valve structure.

We have now found that a lot of improvement and advantages can be achieved if the materials of constructions of the disc occluder, the metallic ring component as well as the supporting ring lugs positioning are judicially constructed.

After a considerable research and investigation it has now been discovered by us that we have been able to achieve considerable advancement in the field by our improved heart valve assembly which has all the advantageous properties.

Thus, according to this invention there is provided an improved heart valve assembly comprising sewing ring component 2, metallic valve housing component 3, and a disc occluder 4, said disc occluder being held tiltably on supports within the enclosed space of the valve housing component, said valve housing component having a grooved ring portion externally and having said sewing ring component accommodated on same, said disc occluder being made of Agate, polyacytel homopolymer, synthetic sapphire, synthetic ruby, corundum or ceramics (alumine, tungsten carbide, titanium carbide or their mixtures) or materials having a coating of one or more of these said ceramic materials.

Such ceramic coated materials can be made of metal e.g. aluminium, titanium, steel or "Stellite" (a cobalt-chromium-tungsten alloy) having a coating of one or more of the ceramic materials mentioned above.

The disc occluder is provided with a substantially flat surface 4b on one side and a substantially tapered surface 4a on the opposite side thereof.

The disc occluder is provided with a centrally depressed portion 4c for engaging it on suitable support means of the valve housing, the said depression being provided on the tapered side of the disc occluder.

The disc occluder is optionally provided with a marginally depressed portion 4d on the substantially flat surface, the said depressed portion being not as prominent as the depression portion on the other side of the disc.

The disc occluder is fabricated by injection moulding or machining or grinding or sintering depending on the type of the material.

The disc occluder is polished to a surface finish of 0.1 micron or better using standard polishing techniques.

According to another feature of this invention and modification, the valve housing is fabricated using "Stellite" (a cobalt-chromium-tungsten alloy) or titanium or alloys of titanium with aluminium vanedium or palladium. The valve housing which is circular in shape has a grooved portion 3d externally for accommodating the sewing ring component while the internal side of the housing is plain.

It has been further discovered by us that the valve housing which is also sometimes called metallic cage component, can also be made from stainless steel or cobalt based alloys either alone or additionally having a coating of Boron Nitride or Titanium Nitride or Diamond.

We have also discovered that the valve housing fabricated from "Stellite", Titanium or Alloys of Titanium with Aluminium, Vanedium or Palladium can also be further strengthened to have more longevity if it is provided with a surface coating of Boron Nitride or Titanium Nitride or Diamond. Such surface coating referred to above can be carried out by subjecting the valve housing as per se known methods such as Boriding, Carbiding, Siliciding which coatings can be applied singularly or in combination. Further Nitriding is also advantageous.

Thus known methods of physical or chemical deposition such as vapour deposition or electro sputtering techniques can be employed.

The valve housing is provided with suitable support means for the disc occluder from both sides of the housing, the said support means being solid members, extending to a distance substantially to the centre of the ring.

The ring is provided with one support means 36 from one end thereof, said support means extending substantially to the centre of the housing and having a hooked portion 3c curved towards the opposite side of the housing.

The housing is also provided with two supporting members 3a on the side opposite to that which is provided with one supporting member, the said two supporting members extending radially substantially to the centre of the housing and being substantially flat members.

The support lugs are independent lugs. The disc is mounted in such a manner that the tapered surface is pointed towards a side of the housing which has the single hooked support lug and wherein the said hook engages the depressed portion of the tapered surface of the disc component such that the disc is mounted tiltably on the said three supports provided in the housing component.

We have achieved tremendous advantages when the three supporting lugs for the disc occluder are spaced at approximately 60° from each other within the circular metallic ring component. This has given a special advantage of dividing the circular space within the ring components into almost two equal passages because the three lugs not only extend towards the centre of the ring component but also terminate close to the centre of the ring component.

The sewing ring component, as the same implies, is in the form of a ring and is fabricated from knitted or woven fabrics of carbon or knitted or woven fabrics of polyester or poly-tetre-fluoroethylene which said fabric may be coated with carbon.

The inner diameter of the sewing ring is normally slightly smaller than the other diameter of the groove formed externally on the valve housing. At the time of assembling the component, the sewing ring is slightly extended being flexible and is then allowed to hold the ring. The housing and sewing ring components are fixed together by heating setting the sewing ring at temperatures of 100°/170° C.

After heat setting the sewing on the valve housing, the occluder disc is slipped into place such that the depressed portion on the tapered surface is engaged by the hooked strut member or lug member.

The whole manufacture of the different components and their assembly is carried out in dust proof environment as per good manufacturing practices for medical devices. The valve assembly is packed in a special plastic container suitable for high pressure steam sterilisation and labelled.

We claim:

1. An improved heart valve assembly comprising a sewing ring component, a valve housing component and a disc occluder, said disc occluder being held tiltably on supports within the enclosed space of the valve housing component, said valve housing component having a grooved ring portion externally and having said sewing ring component accommodated on same and fabricated from knitted or woven fabrics of carbon or knitted or woven fabrics of polyester, polytetrafluoroethylene, which said polyester or polytetrafluoroethylene fabric may be coated with carbon, said valve housing being a fabricated housing of cobalt-chromium-tungsten alloy having a surface coating of Titanium Nitride, said disc occluder being made of material selected from the group consisting of synthetic sapphire wherein the disc occluder is provided with a substantially flat surface on its one side and a substantially convex surface on the opposite side thereof, said convex side being also provided with a centrally depressed portion for engaging it on a suitable support means of the valve housing, said substantially flat surface having a centrally depressed portion being not as prominent as the depressed portion on the other side of the disc, and wherein the valve housing is provided with a plurality of support means for the disc occluder from both sides of the housing, the said support means being solid or strut members extending to a distance substantially to the center of the housing, one support means provided from one side of the housing and having a hooked end portion curved towards the opposite side of the housing adapted to engage the depressed portion on the convex surface of the disc component, two other support means provided on the side of the housing opposite to that which is provided with said one support means, the said two support means extending substantially radially to the center of the housing and being substantially flat members adapted to support the substantially flat surface of the disc occluder such that the disc occluder is mounted tiltably on the said three support means provided in the housing component.

2. An improved heart valve assembly as claimed in claim 1, wherein the disc occluder has a polished surface finish of 0.1 micron or better using standard polishing techniques.

* * * * *